United States Patent [19]

Buck

[11] Patent Number: 5,460,450

[45] Date of Patent: * Oct. 24, 1995

[54] CRYOGENIC HYGROMETER

[76] Inventor: Arden L. Buck, 5995 McSorley La., Boulder, Colo. 80303

[*] Notice: The portion of the term of this patent subsequent to Apr. 5, 2011 has been disclaimed.

[21] Appl. No.: 221,945

[22] Filed: Apr. 1, 1994

Related U.S. Application Data

[63] Continuation-in-part of Ser. No. 906,892, Jun. 30, 1992, Pat. No. 5,299,867.

[51] Int. Cl.⁶ .................................................. G01N 25/02
[52] U.S. Cl. .................................................. 374/20; 374/18
[58] Field of Search ................................ 374/16, 17, 18, 374/19, 20, 45; 73/23.2, 29.01, 29.02, 73, 335

[56] References Cited

U.S. PATENT DOCUMENTS

| | | | |
|---|---|---|---|
| 3,623,356 | 11/1971 | Bisberg | 374/20 |
| 3,812,596 | 5/1974 | Willmanns | 374/20 |
| 4,216,669 | 8/1980 | Harding, Jr. | 73/29.02 |
| 4,629,333 | 12/1986 | Dosoretz et al. | 374/20 |
| 4,826,327 | 5/1989 | Michell | 374/20 |
| 4,946,288 | 8/1990 | Siska et al. | 374/20 |
| 5,022,045 | 6/1991 | Elliott | 374/20 |
| 5,052,818 | 10/1991 | Nishizawa et al. | 374/17 |
| 5,090,817 | 2/1992 | Ker et al. | 374/16 |
| 5,299,867 | 4/1994 | Buck | 374/20 |

FOREIGN PATENT DOCUMENTS

| | | | |
|---|---|---|---|
| 1165544 | 10/1958 | France | 374/20 |
| 813207 | 3/1981 | U.S.S.R. | 374/20 |
| 1188692 | 10/1985 | U.S.S.R. | 374/20 |
| 2036339 | 6/1980 | United Kingdom | 374/19 |
| 2202941 | 10/1988 | United Kingdom | 374/16 |

Primary Examiner—William A. Cuchlinski, Jr.
Assistant Examiner—G. Bradley Bennett
Attorney, Agent, or Firm—Donald W. Margolis; Edwin H. Crabtree

[57] ABSTRACT

A dew or frost point temperature hygrometer wherein a reflective surface, which is cooled by a cryogenic source and held at the dew or frost point temperature by a servo control, reflects light from a light source to a light detector. Very low concentrations of moisture or frost which condense on the reflective surface are measured very rapidly as a change in light reflected from that surface. No re-calibration is needed throughout its exceedingly wide moisture measurement range of from less than 1 part per billion to about 30 parts per thousand within a range of temperature from about −110° C. to about 30° C.

17 Claims, 3 Drawing Sheets

CRYOGENIC HYGROMETER

RELATED APPLICATION

This application is a continuation in part of U.S. Patent Application entitled Low Moisture Cryogenic Hygrometer, by Arden L. Buck, Ser. No. 07/906,892, filed Jun. 30, 1992, now U.S. Pat. No. 5,299,867 issued Apr. 5, 1994.

BACKGROUND OF THE INVENTION (a) Field of the Invention

This invention relates in general to hygrometer apparatus which includes electrical circuitry to measure moisture condensed as dew or frost on a chilled mirror which is cooled by a cryogenic source, and to the method of using the same. More particularly, the invention concerns an apparatus and method for very fast and accurate measurement of moisture in a gas over a wide range of dew or frost point temperatures and gas pressures.

(b) Description of the Prior Art

Hygrometry, the measurement of moisture in gases, has always been important to industrial processes and atmospheric research, but recently the importance of such measurements has increased. As microelectronic feature sizes move into the sub-micrometer realm and super critical fluid extraction based on high-purity carbon dioxide becomes the accepted method for environmental and pharmaceutical extraction, the low parts-per-billion (ppb) moisture range is becoming the maximum acceptable level for moisture and other contaminants in specialty gases.

The aerospace industry has similar moisture contaminant standards for space station systems. Atmospheric moisture measurements are important to understanding the role moisture plays in the chemistry of global warming and ozone depletion.

There has been a continuing effort to increase the sensitivity, accuracy and response time of moisture analyzers, and especially performance of the dew point or frost point temperature chilled mirror hygrometers, to meet these challenges. As is explained in Bisberg U.S. Pat. No. 3,623,356, dew point temperature hygrometers are frequently used to determine the moisture content of a gas sample. Typically a mirror is exposed to the gas sample and cooled to the dew or frost point temperature of the gas. Formation of dew or frost on the mirror is detected by means of a light source and a light sensitive detector responsive to light reflected from the mirror. The detector develops an error signal which is used to control the current to a thermoelectric cooler attached to the mirror, to maintain a predetermined thickness of condensate on the mirror surface. A temperature measuring device attached to the mirror is employed for measuring the temperature of the mirror, thus indicating the dew or frost point temperature of the gas sample. In this reference, the mirror, optics, and electrical circuit constitutes a thermo-optical servo system which functions to maintain a constant reflectance at the mirror surface, hence a condensate equilibrium at the dew or frost point temperature. Its operation is based upon the principle that an equilibrium exists between the water vapor pressure in the atmosphere and a water/ice surface at a unique temperature, the dew/frost-point temperature.

Nishizawa, et al. U.S. Pat. No. 5,052,818 teaches dew point temperature testing only at temperatures of −80° C., or lower (colder). It is directed at overcoming a perceived prior art problem by measuring scattered light rather than reflected light. It developed its technology to circumvent a perception that reflected light from a chilled mirror does not work for a gas having a very low moisture content. To overcome this perceived problem, Nishizawa et al. developed technology that pre-cools the to-be-tested gas, thus forming the moisture into ice crystals which are directed at and impact the mirror through a nozzle, rather than condensing dew or frost. Pre-cooling the to-be-tested gas is necessary for the operation of the Nishizawa, et al. system, so that ice crystals are formed at the reflective surface to scatter the light. This sudden development of ice crystals on the reflective detector surface, causes the light to be scattered, rather than reflected. In order to detect this sudden appearance of ice crystals, Nishizawa et al. must use a focused source of light which detects the presence of the ice crystals by scattering the light, rather than by reflecting unfocused light. Nishizawa et al. has a control system which uses liquid nitrogen in a liquefied gas container which is blown against a cold surface by means of a stop valve and a needle valve. The use of stop valves and needle valves does not work to precisely control cooling, as does, for example a Type 1 servo control system.

Most hygrometers employ two light sources and two photodetectors as coordinated pairs to reduce the effects of temperature on source brightness and/or detector efficiency. One pair provides an output which is proportional to the light which is specularly reflected from the mirror. The other pair provides a reference output which is used to correct for temperature-caused changes.

The most common prior art method for cooling the mirror is thermoelectric, using one or more Peltier junctions, which lowers the surface temperature as a function of applied voltage. Peltier junctions, however, become rapidly less efficient at lower temperatures, and achieving very low frost point temperatures requires massive multistage systems which consume exponentially larger amounts of power as the frost point temperature decreases. With the Peltier junction, it becomes impractical to achieve frost point temperatures much below about −80° C. Further, as frost point temperature becomes lower, the response time of thermoelectrically cooled hygrometer becomes very slow.

Industrial chilled mirror hygrometers commonly utilize thermoelectric cooled mirrors. However, their limited measurement range and slow response makes them less desirable for real-time on line monitoring of moisture levels, especially in the critical area of semiconductor manufacturing.

Cryogenic cooling of the hygrometer mirror as compared to thermoelectric cooling, allows operation to much lower moisture levels, with much faster response time. Cryogenically chilled mirror hygrometers have been developed by Cambridge Systems Inc, the Naval Research Laboratory (NRL), the National Center for Atmospheric Research (NCAR), and others. The cryogenic hygrometers use a cryogen, such as liquid nitrogen or freely boiling Freon 13 chlorofluorocarbon coolant, as the heat sink. In these instruments, generally, a mirror is thermally connected to a cryogenic heat sink by means of a thermally-conductive rod. An electrically resistive coil wound around the thermally-conductive rod provides heating to raise the temperature of the mirror to the dew or frost point temperature. In all of these prior art cryogenic instruments, the thermally-conductive rod is attached to the mirror at one end, and is immersed directly into the cryogen at the other end of the rod. To maintain performance at all levels of cryogen, the rod is inserted horizontally into the cryogen container, most typically a dewar, near the bottom of the container. This requires a container with an orifice created in its body, a complex and costly procedure since the dewar cryogen container typically comprises two nested and spaced apart shells, with the space between them being evacuated to obtain the maximum thermal insulation. Thus, in making a penetrated dewar, the vacuum seal must be broken, an opening formed through both shells, the space between the shells evacuated and resealed. A further complication in the resulting system is the loss of cryogen efficiency due to thermal losses caused by the stem penetration through the dewar. Furthermore, the prior art fixed thermal transfer arrangement, in which a mirror is thermally connected to a cryogenic heat sink by means of a thermo-conductive rod, allows only a limited temperature measurement range over which the instrument can operate in an optimum manner.

In the above noted prior art cryogenic instruments, control of condensation on the mirror is accomplished by a control circuit in which the input voltage corresponds to the moisture condensate level, and in which the output voltage to the heating coil controls the mirror temperature. This is known as a Type Zero proportional control circuit which responds to condensation level (proportional) and the rate of change of condensation (lead). Because it is relatively simple, and because the physical parameters involved vary over the operation range, such a Type Zero proportional control circuit is able to provide effective control over only a limited moisture measurement range. Outside of that range, it becomes slow or subject to oscillation.

Because of these thermal and circuit limitations, the prior art cryogenic instruments have been able to operate only at relatively low frost point temperatures, typically below −10° C. For airborne research at high altitude, this is acceptable. However, these prior art instruments are not capable of functioning accurately and efficiently in the wider ranges of temperature needed to meet modern industrial demands.

DISCLOSURE OF THE INVENTION

It is therefore an object of the present invention to provide improvements to a cryogenic chilled mirror dew or frost point temperature hygrometer, which allow it to operate over a greater dew or frost point range of temperature, under pressure, with faster response time, greater efficiency, and simpler construction than was previously possible.

Another object is to provide a system which controls change and the rate of heat flow between a chilled radiation reflective surface and the cryogenic heat sink.

Another object is to provide a system which controls change and the rate of heat flow between a chilled radiation reflective surface and the cryogenic heat sink by controlling the exposure of the distal end of a thermally conductive rod, which is connected to the radiation reflective surface, to the cryogen, thereby controlling the temperature of the rod and the system over wider ranges of temperature.

An alternative object is to provide a system which controls the rate of heat flow between a chilled radiation reflective surface and the cryogenic heat sink during operation by controlling the conductivity or the size, shape or dimensions of the thermally conductive rod which is connected to the radiation reflective surface.

Yet another alternative object is to provide a system which controls the rate of heat flow from a thermal conductor in contact with a radiation reflective surface by the use of a system for bringing cryogen from a remote location into cooling contact with the thermal conductor.

A more specific object is to provide such a system in which the heat flow from a thermal conductor in contact with a radiation reflective surface is provided by a cryocooler, such as a closed cycle Stirling or Joules-Thompson system.

Another object of the present invention is to provide a dew/frost point temperature hygrometer in which an electronic servo control circuit is utilized which has the means to measure and control the level of moisture condensation on the chilled surface, and which functions over a very wide range of operating conditions, with faster response time than in the prior art.

Another object of the present invention is to provide a dew/frost point temperature hygrometer in which the electronic servo control circuit which is utilized to measure and control the level of moisture condensation on the chilled surface, over a very wide range of operating conditions, with fast response time is a Type 1 servo-mechanical circuit.

Another object of the present invention is to provide a dew/frost point temperature hygrometer in which the sensitivity of the hygrometer is enhanced, especially when measuring very low moisture content, by increasing the pressure of the gas in the sensing chamber, so that for a given dew or frost point temperature capability, an increase in gas pressure provides a proportional increase in sensitivity to fractional moisture content.

To achieve the foregoing objects, and in accordance with the purposes of the invention as embodied and broadly described herein, a dew or frost point temperature hygrometer is provided which includes a thermally conductive dew or frost collecting surface, such as a radiation reflective surface, for example a mirror, which can be cooled to a temperature at which dew or frost is condensed from the gas environment in which it is located onto the thermally conductive radiation reflective surface. The system for cooling the thermally conductive dew or frost collecting surface, such as a radiation reflective surface includes a length of thermally conductive material, such as a rod composed of copper, or other conductive metal, having a length of from about 2 cm to about 6 cm, and a diameter of from about 0.5 cm to about 1.5 cm. The rod constitutes a thermal conductivity path between the mirror and cryogen which is brought into contact with the rod, which path may be varied to effect the efficiency of the temperature control of the mirror surface. Varying the size, shape, and material of the thermally conductive material provides another method of controlling the cooling characteristics of the system. In preferred embodiments, a thermal mass is attached to the rod, for example at its lower end. As detailed below, instead of being immersed in the cryogen, as in the prior art, the metal rod is located remotely from the cryogen, for example, above or in the mouth at the top of a cryogenic container, out of contact with the cryogen, or even more remote from cryogen source, with the cryogen being pumped from its source through conduits to the conductive rod. Where a cryogenic container is used, it may be a standard dewar, which includes a cryogen, such as liquid nitrogen, as a heat sink, rather than a penetrated dewar.

One known in the art device for measuring the mass of condensate which forms on the cooled surface, is a source of radiation, e.g. a light emitting diode (LED), and a radiation detector, such as a photodetector. In such an art known system, a clear mirror, free of any condensed moisture, provides the maximum reflected light for a given radiation source current. Condensation of moisture, in the form of dew at higher temperatures, or frost at lower temperatures, causes a decrease in light reflected from the mirror to the photo detector.

At that time, application of electrical current to the stem heater winding will decrease the moisture condensed on the mirror surface, and move it toward a clear mirror condition. As in the prior art, a device for heating the radiation reflective surface, such as a heat coil, is wrapped around the thermally conductive rod. A system for controlling the rate of thermal transfer between the radiation reflective surface and the cryogen source, which includes, for example, a thermostatic control circuit is provided. The dew or frost point temperature is determined when the reflected light received by the photo detector is decreased by some preset percentage from its steady state clear mirror condition, as determined by a corresponding decrease in the electrical signal output from the detector.

Thermal conduction from the mirror to the cryogen heat sink can be varied during operation by actively changing the dimensions of the rod, the dimensions of the thermal mass at the end of the rod, the proximity of the thermal mass to the cryogen and, in preferred embodiments, the rate of flow of liquid or gaseous cryogen past or through the rod and any associated thermal mass. The advantages of maintaining optimum thermal flow in this manner are that it maintains roughly constant control parameters, allowing the condensate control circuit to be adjusted for optimum speed, sensitivity, and stability performance, and to maintain that performance over a wide range of temperature measurements. It also reduces the usage of cryogen, keeping it to only that which is required for cooling. For instance, when measuring gases which have high dew point temperatures, the temperature at the end of the conductive rod can be raised, since less mirror cooling is required, thus reducing the amount of cryogen which is brought to the rod. It also reduces the usage of cryogen by increasing the efficiency of the cryogen container, as compared to a penetrated container. It also simplifies the construction of the system, as it does not require construction of a custom dewar with side penetration.

As noted above, and detailed below, primary temperature control of the mirror surface is achieved by control of a heating element which is associated with the rod which is in thermally conductive contact with the mirror. Cooling temperature control of the thermal mass end of the rod is achieved by control of the quantity of cryogen permitted to contact or flow in proximity to the rod or thermal mass from a remote source of cryogen.

In preferred embodiments, means are also provided for controlling sample gas pressure at the reflective surface. Moisture detection sensitivity can be increased by increasing the sample pressure. This is achieved by installing the sensing chamber within a high pressure sample line and maintaining the flow of the gas through the sensing chamber.

The process of the present invention measures dew/frost point temperature in gases having low levels of moisture using the system of the present invention which, in preferred embodiments, includes at least a thermally conductive reflective surface, for collecting dew or frost, a mechanism for causing a to-be-tested gas to be passed over said reflective surface, a source of cryogenic cooling normally located out of contact with said reflective surface, a heating device associated with said reflective surface, a temperature sensing element associated with said reflective surface, a control circuit, a light source and a reflected light detector. Then, in the practice of the process, a to-be-tested gas is caused to flow over said reflective surface, while directing light from the light source onto the reflective surface. The intensity of the light which is reflected from the reflective surface is measured using the light detector. The cryogenic source is then brought into thermally conductive contact with the reflective surface to cool the reflective surface to at least the dew/frost point temperature of the to-be-tested gas. In alternative embodiments, the heat flow from the thermal conductor in contact with the radiation reflective surface is provided by a cryocooler, such as a closed cycle Stirling or Joules-Thompson system. When the intensity of the light reflected from the reflective surface is reduced, and then determined to be constant, this is taken as an indication that moisture or frost has been collected on the reflective surface, and that the dew/frost point temperature of the to-be-tested gas has been reached. The control circuit is used, as appropriate, to activate the source of cryogenic cooling or the heating device in order to hold the reflective surface at the temperature at which the reduced intensity of the reflected light is constant, which temperature is the dew/frost point temperature. The process can be used to determine dew/frost point temperatures of the to-be-tested gas in the range of from about −110° C. to about 30° C., and under a pressure of from about 0.5 atmosphere to about 100 atmospheres, and wherein moisture is present in the to-be-tested gas from less than one part per billion by volume of the gas to over 30 parts per thousand.

One benefit of the present invention is due to the fact that dew or frost point temperature is a fundamental and direct measurement, which needs no calibration, except the temperature measurement. This is due to the fact that dew or frost point temperature is defined as the temperature at which dew or frost appears. Since dew or frost point temperature is measured by measuring the temperature at which the dew or frost condenses upon the chilled mirror, no calibration is required. In preferred embodiments, an ultrastable thermistor imbedded in the radiation reflective element measures the dew or frost point temperature.

In preferred embodiments, high detection sensitivity of the cryogenic dew or frost point temperature hygrometer of the present invention is enhanced through design and application of a Type 1 Servo System which permits operation with a controlled, substantially constant dew or frost layer. As detailed below, this is accomplished by integrating the photo detector output which is indicative of the dew or frost layers to achieve control of the heating and cooling cycle, as detailed below.

While a mirror type of condensation detector is currently preferred, other known in the art condensation measuring systems, such as measurement of capacitance or other electrical property of the surface, the propagation velocity of an acoustic wave traveling across the surface, or the resonant frequency of a vibrating crystal in contact with or containing the cooled surface, as well as other condensation measuring systems may be used in the practice of the present invention.

These and other objects of the present invention will become apparent to those skilled in the art from the following detailed description, showing the contemplated novel construction, combination, and elements as herein described, and more particularly defined by the appended claims, it being understood that changes in the precise embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments of the present invention according to the best modes presently devised for the practical application of the principles thereof, and in which.

DESCRIPTION OF THE PREFERRED EMBODIMENTS

Figure 1:
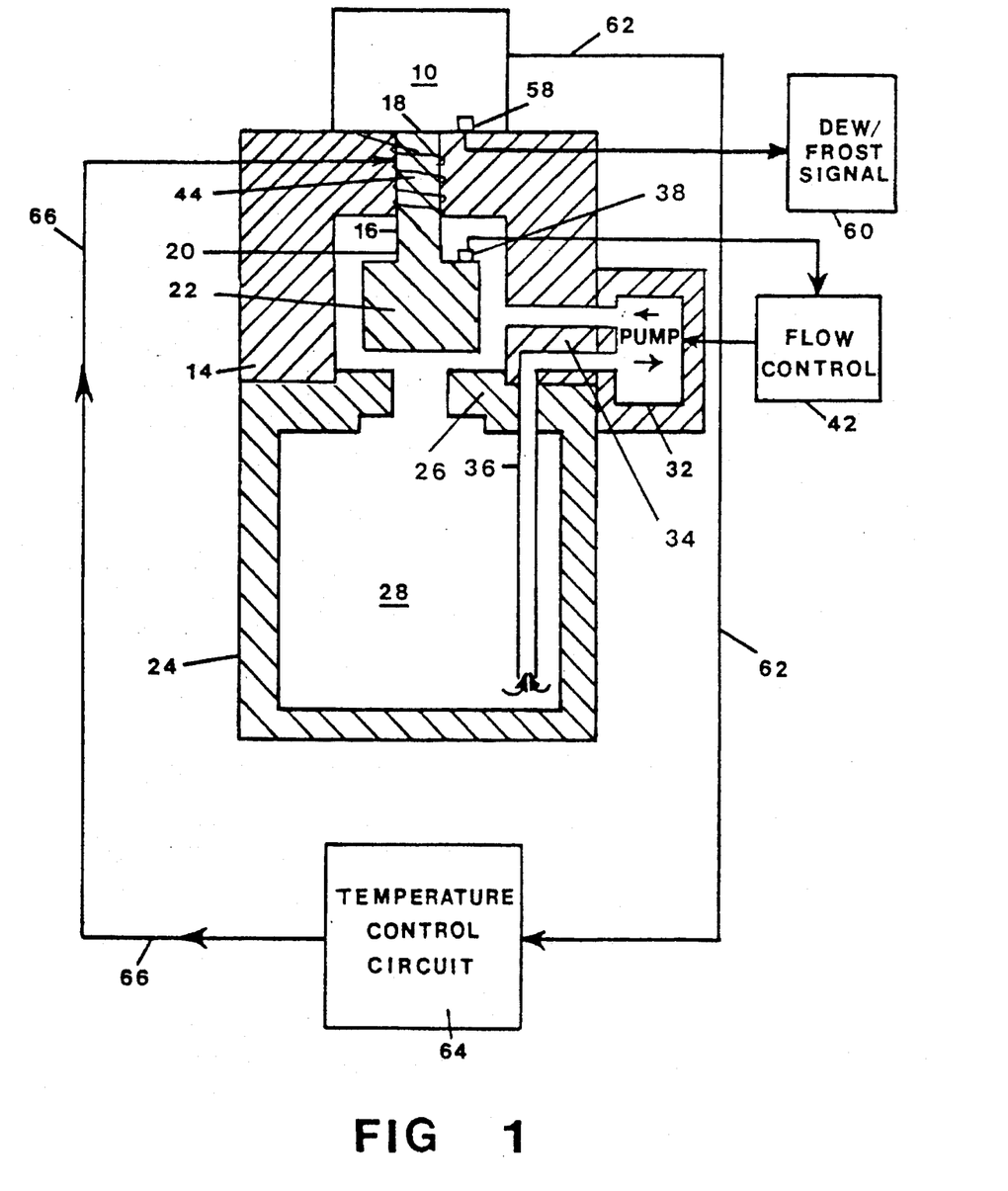
FIG. 1 provides a generalized block diagram, partially in cross-section, of a cryogenic dew or frost point temperature hygrometer which incorporates the present invention.

FIG. 1 provides a block diagram, partially in cross-section, of a preferred embodiment of the present invention. As shown in FIG. 1, a cryogenically cooled dew/frost point temperature measuring system 10 containing a condensation collecting surface, in which an optical detection system, a quartz micro-balance system, a capacitance measurement system, a system for measuring the propagation velocity of an acoustic wave traveling across the surface, or a system for measuring the resonant frequency of a vibrating crystal either in contact with or containing the cooled surface, as well as other electrical or physical property measurements, may be used in the practice of the present invention to determine the amount of condensation.

Figure 2:
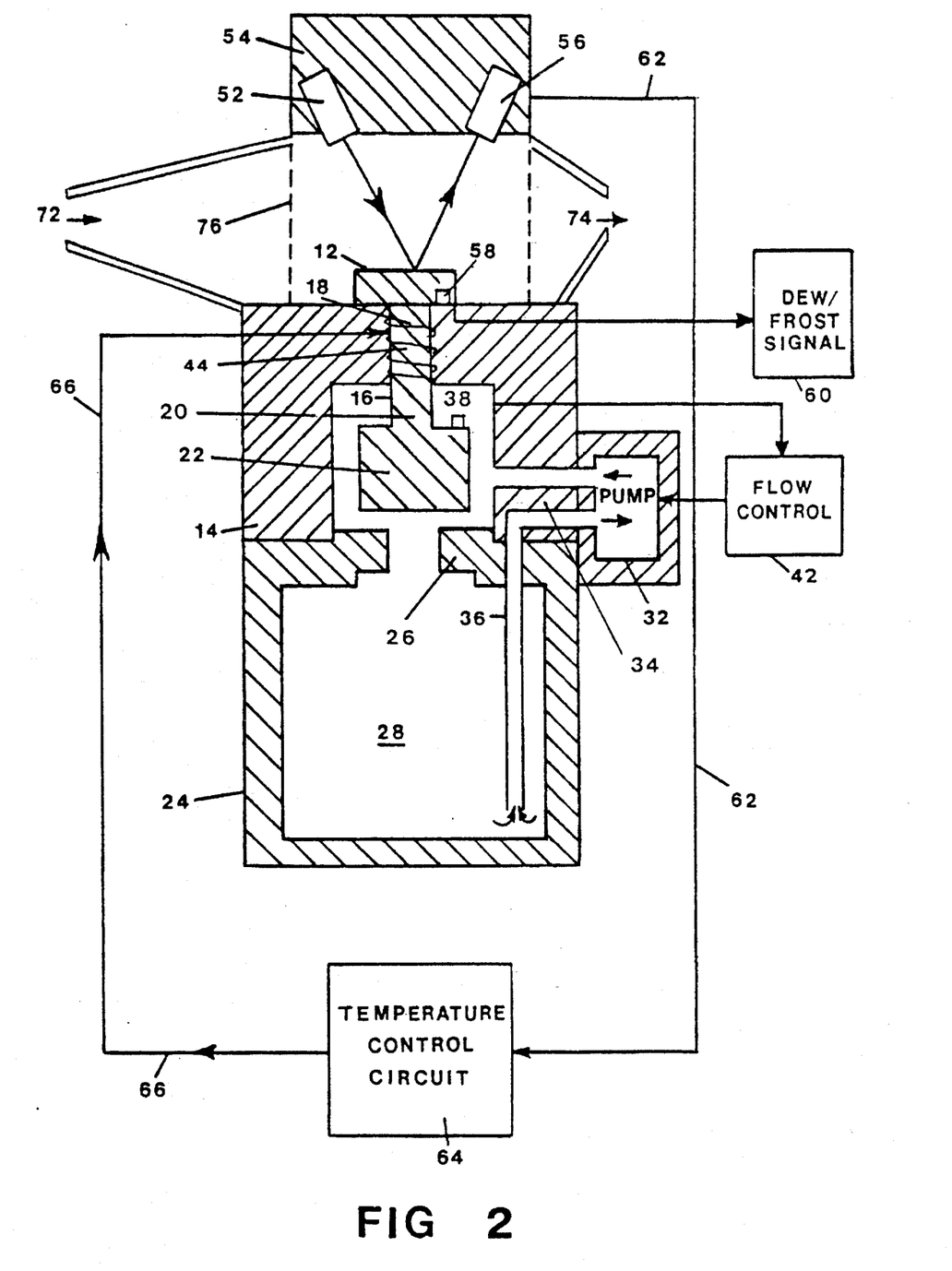
FIG. 2 provides an enlarged cross-section, of a cryogenic dew or frost point temperature hygrometer which shows the details of a system which utilizes a frost or dew point temperature sensing apparatus which includes in combination a radiation source, a radiation reflector, and a radiation detector, and which also includes a cowling structure which allows the pressure of the gas which is being analyzed to be increased.

As shown in FIG. 2, in preferred embodiments, a thermally conductive radiation reflecting element 12, for example in the form of a mirror, is supported by a downwardly open structural container, generally 14. Mirror 12 is constructed, for example, of gold or rhodium plated copper which assures a uniform temperature across its surface. Structural container 14 is composed primarily of insulating material, or is otherwise constructed to provide insulation of the materials within and below structural container 14. A thermally conductive rod 16 extends through an opening in the top of structural container 14, which rod 16 has a proximal end 18 which is in thermally conductive contact with mirror 12. Distal end 20 of rod 16 carries a mass of thermally conductive material 22 within the open portion of structural container 14. The opening in the top of structural container 14 through which rod 14 extends fits snugly around rod 16 in a substantially gas tight manner.

An insulated liquid container 24, such as a standard dewar, having open mouth 26 resides below and supports, and is in insulating, substantially gas tight closed contact with the bottom of structural container 14. In operation, as further detailed below, insulated container 24 will contain a liquid cryogen 28, such as liquid nitrogen or Freon 13 chlorofluorocarbon.

As shown in FIG. 1, in operation, the distal end 18 of rod 16, and the mass of thermally conductive material 22 are normally out of direct contact with cryogen 28. The distal end 18 of rod 16, and the mass of thermally conductive material 22 are brought into contact with cryogen 28 by the flow of cryogen 28 up through mouth 26 of container 24 or from a pump 32. This flow of cryogen 28 is activated and controlled by a pump 32. Pump 32 has an outlet connection 34 into the open space portion of structural container 14, and an inlet connection 36 into insulated container 24. The inlet and outlet functions may be reversed, and inlet 36 moved to dewar mouth 26, and still operate to bring cryogen to the distal end 18 of rod 16, and the mass of thermally conductive material 22. As detailed below, pump 32 can be activated to initiate or to regulate the rate of flow of cryogen 28 to the mass of thermally conductive material 22 and rod 16 when cooling of mirror 12 is required.

In alternative embodiments, the heat flow from the thermally conductive material 22 which is in contact with reflecting element 12 is provided by a cryocooler, such as a closed cycle Stirling or Joules-Thompson system.

The need for cooling of mirror 12 is indicated by temperature sensor 38 which is in thermally conductive contact with rod 16 or thermal mass 22. Temperature sensor 38 can cause a heat flow control circuit 42 to call for increased activity of pump 32 to bring cryogen into the opening of structural container 14. The flow of cryogen is maintained in such a way as to provide roughly optimum thermal flow characteristics to mass 22 and to rod 14. In this preferred embodiment, optimum thermal flow characteristic is considered to be a constant temperature maintained in the distal area 20 of rod 16. Such constant temperature can be maintained by manually switching control circuit 42 to different control points for different dew or frost point temperature operating ranges, or it can be maintained automatically. In either case, it is desirable to maintain control in a slower and less precise manner than the control of mirror temperature via the condensate control circuit, as detailed below.

A heating element 44, such as a heating coil, is connected to rod 16, preferably adjacent mirror 12, for selectively heating rod 16 and connected mirror 12, also as detailed below.

Radiation source 52, such as an LED, supported by a mounting assembly 54 is positioned to illuminate mirror 12, while radiation detector 56, such as a photodetector, also supported by mounting assembly 54 is positioned to receive light reflected from mirror 12. The combination of the radiation source 52, mounting assembly 54 and detector 56 is referred to as the optics block. As detailed below, and as taught by the prior art, condensation of moisture or frost on mirror 12 causes light from source 52 to be scattered or absorbed, thereby reducing the amount of reflected light reaching detector 56. A temperature sensing device 58, such as a thermistor, is in thermal contact with mirror 12 to indicate the dew point or frost point temperatures to output device 60.

While not shown in FIG. 1, as is well known in the art, a second light source directed to a second photodetector serves as a reference to provide correction for any thermally induced changes in the behavior of mirror 12, primary light 52, or detector 56.

Signals 62 from detector 56 are brought to temperature control circuit 64, which generates heater control signal 66 to control heat element 44 in order to maintain a constant level of condensate on the surface of mirror 12, regardless of changes in dew or frost point temperature. As noted above, temperature sensor 58, imbedded in mirror 12 provides an output signal 60 to indicate the dew or frost point temperature.

Referring again to FIG. 2, in preferred embodiments, the to-be-tested gas input line 72 and gas output line 74 are connected to a gas tight cowling 76 which totally surrounds mirror 12, radiation source 52 and radiation detector 56. As detailed below, the cowling structure 76 allows the pressure of the gas which is being analyzed to be increased, for example to 5, or as to as much as 100 atmospheres. By increasing the pressure, the sensitivity of the process and apparatus are increased.

In operation, the to-be-tested gas is caused to flow past mirror 12, for example through gas input line 72 connected to an air tight cowling 76 which totally surrounds mirror 12. Mirror 12 is normally initially at a temperature above the dew/frost point temperature of the to-be-tested gas. Radiation source 52 is activated at a given voltage, and radiation impinges on radiation reflecting mirror 12 and the clear mirror level of reflected radiation is "read" by radiation detector 56, and output as an initial voltage. Pump 32 is activated by heat flow control circuit 42 to bring cryogen 28 up from insulated liquid container 24 into the opening of structural container 14, thereby contacting the mass of thermally conductive material 22, and perhaps the distal end 18 of rod 16, and cooling them both. Thermally conductive rod 16, which has a proximal end 18 in thermally conductive contact with mirror 12 thus induces mirror 12 to also be cooled until it reaches the dew or frost point temperature of the gas environment.

As condensate forms on the surface of mirror 12, the reflected radiation is scattered and absorbed, and detector 56 "reads" a lower intensity level of radiation, and thus transmits a lower voltage which is indicative of the initial formation of condensate on the surface of the mirror.

As the condensate on the mirror 12 thickens, the intensity of the radiation which detector 56 "reads" continues to lower, and in turn transmits a still lower voltage. When the thickness of the condensate exceeds the level at which the instrument is set to operate, as determined by the level of radiation which detector 56 senses and the voltage which it transmits, detector 56 provides an error signal to temperature control circuit 64. Control circuit 64 then activates heating coil 44, which heats rod 16 to thereby increase the temperature of the surface of mirror 12 in a manner such that the condensate level is reduced until it returns to a preset level, as read by detector 56. Condensate level is thus retained at substantially preset operating level, regardless of the changes in dew or frost point temperature of the gas which is being tested. Simultaneously, temperature sensor 58 provides a reading of the temperature of mirror 12, and that reading is output as the dew or frost point temperature to signal 60.

In a similar manner, pump 32 will be activated to initiate or to increase the rate of flow of cryogen 28 to the mass of thermally conductive material 22 and rod 16 when additional cooling of mass 22 is required. The need for the cooling of mass 22 is indicated by temperature sensor 38. When the temperature of mass 22 is raised beyond that called for by controller 42, the flow of cryogen is increased to provide additional cooling to mass 22 and to rod 14 to maintain a substantially constant temperature in the distal area 20 of rod 16. As indicated above, the temperature of mass 22 can be selected by manually switching control circuit 42 to different control points for different dew or frost point temperature operating ranges, or it can be maintained automatically. Because the temperature of mass 22 is not a critical function of the dew or frost point measurement process, the cooling control is preferably maintained at a slower speed and in a less precise manner than the control of mirror temperature via the heating coil 44 temperature control circuit 64.

In preferred operations of the present invention, the to-be-tested gas input 72 and gas output lines are connected to a solid cowling 76 which totally surrounds mirror 12, radiation source 52 and radiation detector 56, as shown in FIG. 2. The pressure of the gas which is being analyzed can be increased within cowling structure 76 to almost any pressure, but 100 atmospheres appears to be a practical upper limit. In preferred embodiments gas pressures in the range of from about 1 atmosphere to about 5 atmospheres are most likely to be used. By increasing the pressure, the number of water, or other to-be-tested condensate molecules, are increased in cowling 76, thereby increasing the sensitivity of the process and apparatus. For a given dew or frost point temperature capability, an increase in gas pressure provides a proportional increase in sensitivity to fractional moisture content.

Alternative means to measure the amount of condensation on the chilled mirror surface, other than the optical reflectance method embodied in prior art, may take the form of measurement of capacitance or other electrical properties of the surface; measuring the propagation velocity of an acoustic wave traveling across the surface; or the resonant frequency of a vibrating crystal in contact with or containing the surface, and by other means.

Figure 3:
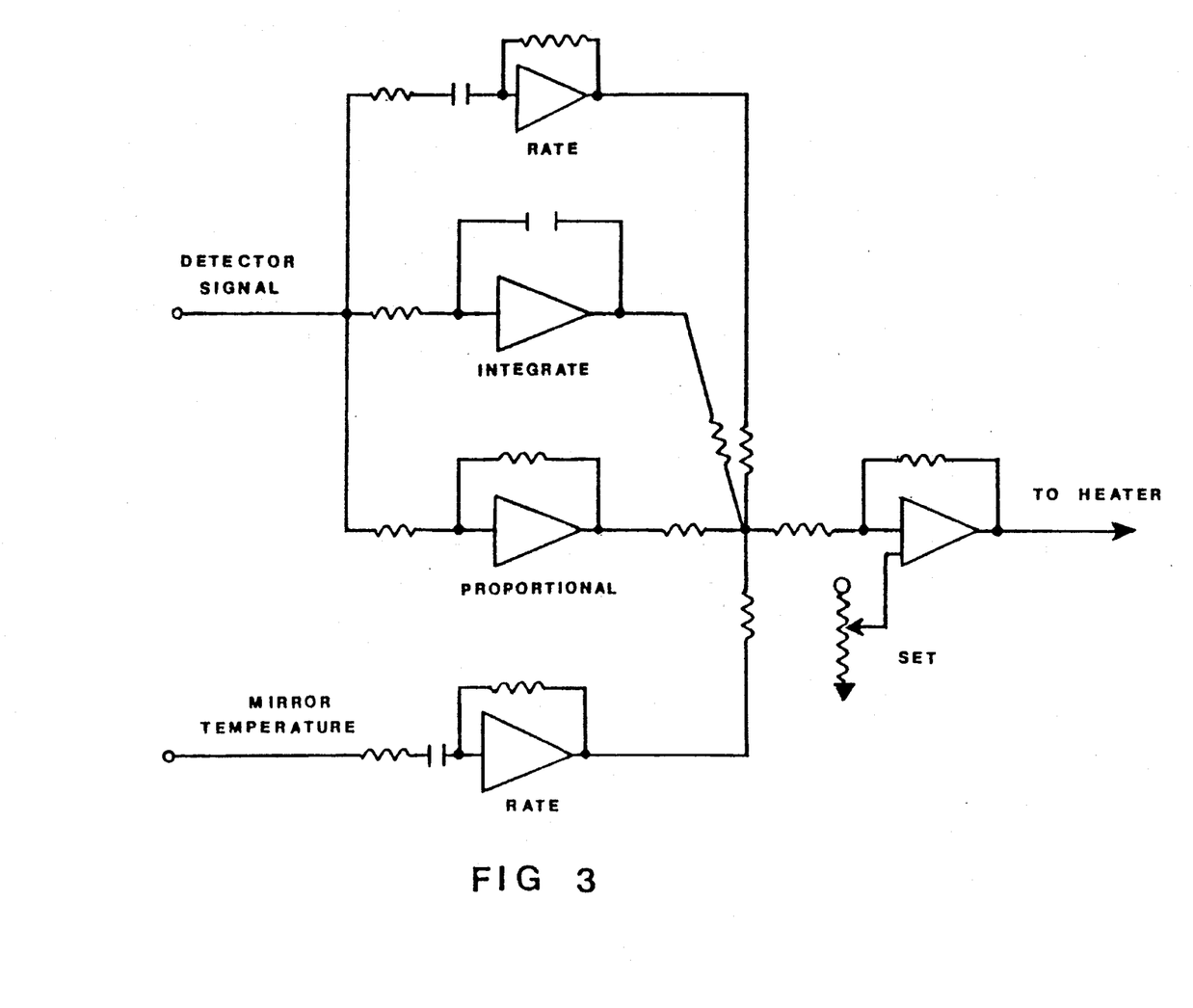
FIG. 3 is a schematic diagram setting forth an example of one kind of Type 1 servo system which may be used in the present invention to control the amount of condensate which is present on radiation reflecting surface.

FIG. 3 provides a self explanatory schematic diagram setting forth an example of one kind of Type 1 servo system which may be used in the present invention to control the amount of condensate which is present on radiation reflecting surface 12.

As taught above, operation of a hygrometer which has a dew or moisture collecting surface is based on the control of the dew or moisture collecting surface temperature in a manner such that a constant layer of dew or frost condensation is maintained at that surface. The temperature of the surface at which a constant layer of dew or frost condensation is maintained is then the dew or frost point temperature of the gas which is being measured, and is the desired output quantity which the hygrometer measures. The normal method for initially acquiring the necessary constant condensate layer upon start up of the hygrometer instrument is to allow the surface to cool under normal servo control, and remain cool until it has acquired sufficient moisture from the gas stream to come into proper servo control. At high frost point temperatures, this typically occurs within seconds of start up. However, at very low frost point temperatures, acquiring the appropriate layer can take minutes or hours, due to the low water vapor content of the gas stream. In one process of the practice of the present invention, the start up period can be greatly accelerated by introducing moisture from another source, which moisture is in excess of that which occurs in the to-be-tested gas stream into the sensing area. This greatly increases the amount of water which is present and available to be picked up by the dew or moisture collecting surface, and thus allows the layer to be acquired quickly, thereby also allowing normal operation of the system and process to be initiated much more quickly.

The method for introducing excess moisture can take one of several forms. In one method, a known quantity of water can be injected into the gas stream entering the sensing area of the hygrometer in a single pulse. In another method, moisture can be continuously injected into the sensing area of the hygrometer until the frost layer is acquired. The gas stream can be moistened for a period of time by routing the incoming gas through a moisture-containing absorptive material, or by allowing ordinary room air to merge into the sensing area without flow taking place, or by injecting moist gas from a permeation tube which is connected to the incoming gas line.

While the invention has been particularly shown, described and illustrated in detail with reference to the preferred embodiments and modifications thereof, it should be understood by those skilled in the art that equivalent changes in form and detail may be made therein without departing from the true spirit and scope of the invention as claimed, except as precluded by the prior art.

The embodiments of the invention for which an exclusive privilege and property right is claimed are defined as follows:

1. A hygrometer system for detecting and monitoring moisture in a gas as a function of the dew or frost point temperature of the moisture in the gas throughout a wide range of temperatures and pressures, comprising in combination:

a dew or moisture collecting surface;

means for cooling said dew or moisture collecting surface to its dew or frost point temperature, said cooling means normally being out of contact with said dew or moisture collecting surface and any thermally conductive element which is in thermally conductive contact with said dew or moisture collecting surface;

means for controllably and precisely bringing said cooling means into contact with said dew or moisture collecting surface or into contact with a thermally conductive element which is in thermally conductive contact with said dew or moisture collecting surface;

means for heating said dew or moisture collecting surface when it is cooler than its dew or frost point temperature;

means for monitoring the formation of dew or frost at said dew or moisture collecting surface;

means for monitoring the temperature of said dew or moisture collecting surface to indicate when the dew or frost point temperature of the gas which is being monitored is reached; and means for continuously controlling the thermal flow characteristics between the cooling means and the heating means and the dew or moisture collecting surface; whereby moisture in a gas is detected and monitored as a function of the dew or frost point temperature of the gas.

2. The hygrometer system of claim 1 for detecting and monitoring moisture in a gas wherein said cooling means is a cryogen.

3. The hygrometer system of claim 2 for detecting and monitoring moisture in a gas wherein said means for controllably bringing said cryogen cooling means into contact with said dew or moisture collecting surface or into contact with any thermally conductive element which is in thermally conductive contact with said dew or moisture collecting surface includes a pump.

4. The hygrometer system of claim 1 for detecting and monitoring moisture in a gas wherein said means for continuously controlling the thermal flow characteristics between the cooling means and the heating means and the dew or moisture collecting surface includes a Type 1 Servo system.

5. The hygrometer system of claim 1 for detecting and monitoring moisture in a gas wherein means for pressurizing the gas in the vicinity of the dew or moisture collecting surface are included.

6. The hygrometer system of claim 5 for detecting and monitoring moisture in a gas wherein said means for pressurizing the gas in the vicinity of the dew or moisture collecting surface are capable of pressurizing the gas to a pressure of up to about 100 atmospheres.

7. A hygrometer system for detecting and monitoring moisture content of less than 1 part per billion by volume, of a to-be-tested gas, as a function of the dew or frost point temperature of the moisture in the to-be-tested gas within a range of from about $-110°$ C. to about $30°$ C. and a pressure range of up to about 100 atmospheres, comprising in combination:

a dew or moisture collecting surface;

means for causing to-be-tested gas to flow over said dew or moisture collecting surface;

gas tight means for enclosing said dew or moisture collecting surface so that to-be-tested gas which flows over said dew or moisture collecting surface can be pressurized in the vicinity of said dew or moisture collecting surface, whereby an increase in gas pressure above the ambient provides a proportional increase in the sensitivity of said dew or moisture collecting surface to the moisture content of the to-be-tested gas;

cryogenic cooling means, said cryogenic cooling means normally being out of thermally conductive contact with said dew or moisture collecting surface, and normally also being out of thermally conductive contact with any thermally conductive element which is in thermally conductive contact with said dew or moisture collecting surface;

means for controllably and precisely bringing said cryogenic cooling means into thermally conductive contact with said dew or moisture collecting surface or into contact with any thermally conductive element which is in thermally conductive contact with said dew or moisture collecting surface;

means for monitoring the formation of dew or frost from a to-be-tested gas on said dew or moisture collecting surface;

means for monitoring the temperature of said dew or moisture collecting surface to indicate what the temperature is when the dew or frost point temperature of a to-be-tested gas which is being monitored is reached;

means for heating said dew or moisture collecting surface when it is below its dew or frost point temperature;

means for continuously and precisely controlling the thermal flow characteristics between said means for controllably bringing said cryogenic cooling means into thermally conductive contact with said dew or moisture collecting surface or any thermally conductive element and the heating means at the dew or moisture collecting surface; whereby, moisture content in the range of from about 1 part per billion to about 30 parts per thousand, by volume, of the to-be-tested gas, is detected and monitored as a function of the dew or frost point temperature of the moisture in the to-be-tested gas within a range of from about $-110°$ C. to about $30°$ C.

8. The apparatus of claim 7 wherein said dew or moisture collecting surface is reflective, a light source for projecting light toward said reflective dew or moisture collecting surface is provided, and said means for monitoring the formation of dew or frost at said reflective dew or moisture collecting surface measures a constant intensity of reflected light from said reflective surface when moisture or frost has collected on the reflective surface at the dew/frost point temperature of the to-be-tested gas.

9. The apparatus of claim 8 wherein said light source does not project focused light on to said reflective dew or moisture collecting surface.

10. The apparatus of claim 7 wherein the to-be-tested gas is not pre-cooled to a temperature slightly higher than the dew point temperature of the to-be-tested gas before the to-be-tested gas is caused to flow over said reflective surface.

11. The process of measuring dew/frost point temperature at low levels of moisture using a system which includes, in combination a reflective surface for collecting dew or frost, means for causing a to-be-tested gas to be passed over said reflective surface, a source of cryogenic cooling normally located out of contact with said reflective surface, heating means associated with said reflective surface, a temperature sensing element associated with said reflective surface, a control circuit, a light source and a reflected light detector, including the steps of:

causing a to-be-tested gas to flow over said reflective surface, directing light from said light source onto said reflective surface;

using said light detector to measure the intensity of the light which is reflected from said reflective surface;

bringing said cryogenic source into thermally conductive contact with said reflective surface to cool said reflective surface to at least the dew/frost point temperature of the to-be-tested gas at which the intensity of the reflected light is reduced;

determining when the intensity of the light reflected from the reflective surface is constant, as an indication that it has been cooled to the dew/frost point temperature and has moisture or frost collected on its surface;

in response to the control circuit, using said heating means to warm said reflective surface;

using said control circuit to hold said reflective surface at the dew/frost point temperature at which the reduced intensity of the reflected light is constant, and, therefore the moisture or frost is collected on said reflective surface is constant;

using the temperature of the reflective surface at which the reduced intensity of the reflected light is constant as an indication of the moisture/humidity of the to-be-tested gas.

12. The process of claim 11 wherein the dew/frost point temperature of the environment is in the range of from about −110° C. to about 30° C.

13. The process of claim 12 wherein the gas environment which is undergoing testing is at a pressure of from about 0.5 atmosphere to about 100 atmospheres.

14. The process of claim 11 wherein moisture is present in the to-be-tested gas from as little as about one part per billion by volume of the gas to about 30 parts per thousand.

15. The process of claim 11 wherein moisture is introduced from another source before the to-be-tested gas is allowed to flow over said reflective surface, to thereby increase the amount of water which is present and available to be picked up by said reflective surface, and thus allowing said reflective surface to quickly, acquire a layer or moisture or frost to be collected on said reflective surface, and thereby also allowing normal operation of the process to be quickly initiated.

16. The process of claim 15 wherein a known quantity of water is injected into the gas stream entering the sensing area of the hygrometer in a single pulse.

17. The process of claim 15 wherein water vapor is continuously injected into the sensing area of the hygrometer until a moisture or frost layer is formed on said reflective surface.

* * * * *